(12) United States Patent
McCabe (10) Patent No.: US 7,398,870 B2
(45) Date of Patent: Jul. 15, 2008

(54) ARTICLE TRANSFER AND PLACEMENT APPARATUS

(75) Inventor: John A. McCabe, Sheboygan Falls, WI (US)

(73) Assignee: Curt G. Joa, Inc, Sheboygan Falls, WI (US)

( * ) Notice: Subject to any disclaimer, the term of this patent is extended or adjusted under 35 U.S.C. 154(b) by 225 days.

(21) Appl. No.: 11/244,378

(22) Filed: Oct. 5, 2005

(65) Prior Publication Data

US 2007/0074953 A1   Apr. 5, 2007

(51) Int. Cl.
*B65G 47/24* (2006.01)
(52) U.S. Cl. ............................. 198/377.08; 198/471.1
(58) Field of Classification Search ............ 198/377.08, 198/471.1, 689.1; 156/552, 568
See application file for complete search history.

(56) References Cited

U.S. PATENT DOCUMENTS

| | | | |
|---|---|---|---|
| 1,393,524 A | 10/1921 | Grupe | |
| 1,605,842 A | 11/1926 | Jones | |
| 1,957,651 A | 5/1934 | Joa | |
| 2,128,746 A | 8/1938 | Joa | |
| 2,131,808 A | 10/1938 | Joa | |
| 2,164,408 A | 7/1939 | Joa | |
| 2,167,179 A | 7/1939 | Joa | |
| 2,171,741 A | 9/1939 | Cohn et al. | |
| 2,213,431 A | 9/1940 | Joa | |
| 2,254,290 A | 9/1941 | Joa | |
| 2,254,291 A | 9/1941 | Joa | |
| 2,282,477 A | 5/1942 | Joa | |
| 2,286,096 A | 6/1942 | Joa | |
| 2,296,931 A | 9/1942 | Joa | |
| 2,304,571 A | 12/1942 | Joa | |
| 2,324,930 A | 7/1943 | Joa | |
| 2,345,937 A | 4/1944 | Joa | |
| 2,466,240 A | 4/1949 | Joa | |
| 2,481,929 A | 9/1949 | Joa | |
| 2,510,229 A | 6/1950 | Joa | |
| 2,591,359 A | 4/1952 | Joa | |

(Continued)

FOREIGN PATENT DOCUMENTS

CA           1146129           5/1983

(Continued)

OTHER PUBLICATIONS

Reciprocating Mechanisma, Ingenious Mechanisms for Designers and Inventors, Franklin Jones vol. 1.

*Primary Examiner*—James R. Bidwell
(74) *Attorney, Agent, or Firm*—Ryan Kromholz & Manion, S.C.

(57) ABSTRACT

An apparatus for transferring articles such as absorbent cores or disposable diaper chassis components from a rotary mechanism, such as a pad turner, to a linear mechanism, such as a conveyor, for further processing. The invention provides a device for picking an article from the outside of a toroidal surface, thence extending transversely under tension the article to be transferred so that at the point of deposition the article is held flat and at full length. Further, the invention allows for apparatus to match the velocity of both the first and second transfer points, even if these velocities are not the same. The device is of particular benefit where an article to be transferred is subject to internally biasing elastic forces.

10 Claims, 5 Drawing Sheets

U.S. PATENT DOCUMENTS

| | | |
|---|---|---|
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,780,253 A | 2/1957 | Joa |
| 2,839,059 A | 6/1958 | Joa |
| 2,842,169 A | 7/1958 | Joa |
| 2,875,724 A | 3/1959 | Joa |
| 2,939,461 A | 6/1960 | Joa |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,203,419 A | 8/1965 | Joa |
| 3,230,955 A | 1/1966 | Joa et al. |
| 3,268,954 A | 8/1966 | Joa |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,521,639 A | 7/1970 | Joa |
| 3,526,563 A | 9/1970 | Schott Jr. |
| 3,538,551 A | 11/1970 | Joa |
| 3,540,641 A | 11/1970 | Besnyo et al. |
| 3,575,170 A | 4/1971 | Clark |
| 3,635,462 A | 1/1972 | Joa |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,772,120 A | 11/1973 | Radzins |
| 3,796,360 A | 3/1974 | Alexeff |
| 3,816,210 A | 6/1974 | Aoko et al. |
| 3,883,389 A | 5/1975 | Schott Jr. |
| 3,888,400 A | 6/1975 | Wiig |
| 3,904,147 A | 9/1975 | Taitel et al. |
| 3,960,646 A | 6/1976 | Wiedamann |
| 4,003,298 A | 1/1977 | Schott, Jr. |
| 4,009,814 A | 3/1977 | Singh |
| 4,009,815 A | 3/1977 | Ericson et al. |
| 4,056,919 A | 11/1977 | Hirsch |
| 4,081,301 A | 3/1978 | Buell |
| 4,094,319 A | 6/1978 | Joa |
| 4,106,974 A | 8/1978 | Hirsch |
| 4,108,584 A | 8/1978 | Radzins et al. |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,215,827 A | 8/1980 | Roberts et al. |
| 4,222,533 A | 9/1980 | Pongracz |
| 4,223,822 A | 9/1980 | Clitheroe |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,342,206 A | 8/1982 | Rommel |
| 4,364,787 A | 12/1982 | Radzins |
| 4,374,576 A | 2/1983 | Ryan |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisneski et al. |
| 4,701,239 A | 10/1987 | Craig |
| 4,726,876 A * | 2/1988 | Tomsovic, Jr. ............... 156/552 |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,795,510 A | 1/1989 | Wittrock et al. |
| 4,801,345 A | 1/1989 | Dussaud et al. |
| 4,802,570 A | 2/1989 | Hirsch et al. |
| 4,840,609 A | 6/1989 | Jones et al. |
| 4,880,102 A * | 11/1989 | Indrebo ................... 198/471.1 |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,925,520 A | 5/1990 | Beaudoin et al. |
| 4,927,322 A | 5/1990 | Schweizer et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 5,000,806 A | 3/1991 | Merkatoris et al. |
| 5,021,111 A | 6/1991 | Swenson |
| 5,025,910 A * | 6/1991 | Lasure et al. .......... 198/377.04 |
| 5,045,039 A | 9/1991 | Bay |
| 5,080,741 A | 1/1992 | Nomura et al. |
| 5,096,532 A | 3/1992 | Neuwirth et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,195,684 A | 3/1993 | Radzins |
| 5,213,645 A | 5/1993 | Nomura et al. |
| 5,223,069 A | 6/1993 | Tokuno et al. |
| 5,226,992 A | 7/1993 | Morman |
| 5,246,433 A | 9/1993 | Hasse et al. |

| | | | | | | |
|---|---|---|---|---|---|---|
| 5,267,933 | A | 12/1993 | Precoma | 6,605,173 | B2 | 8/2003 | Glaug et al. |
| 5,308,345 | A | 5/1994 | Herrin | 6,648,122 | B1 * | 11/2003 | Hirsch et al. ............ 198/377.08 |
| 5,340,424 | A | 8/1994 | Matsushita | 6,649,010 | B2 | 11/2003 | Parrish et al. |
| 5,407,513 | A | 4/1995 | Hayden et al. | D497,991 | S | 11/2004 | Otsubo et al. |
| 5,415,649 | A | 5/1995 | Watanabe et al. | 6,820,671 | B2 | 11/2004 | Calvert |
| 5,421,924 | A | 6/1995 | Ziegelhoffer et al. | 6,837,840 | B2 | 1/2005 | Yonekawa et al. |
| 5,424,025 | A | 6/1995 | Hanschen et al. | 6,875,202 | B2 | 4/2005 | Kumasaka et al. |
| 5,449,353 | A | 9/1995 | Watanabe et al. | 7,077,393 | B2 | 7/2006 | Ishida |
| 5,464,401 | A | 11/1995 | Hasse et al. | 2001/0017181 | A1 | 8/2001 | Otruba et al. |
| 5,494,622 | A | 2/1996 | Heath et al. | 2002/0046802 | A1 | 4/2002 | Tachibana et al. |
| 5,540,647 | A | 7/1996 | Weiermann et al. | 2002/0059013 | A1 | 5/2002 | Rajala et al. |
| 5,545,275 | A | 8/1996 | Herrin et al. | 2003/0000620 | A1 | 1/2003 | Herrin et al. |
| 5,545,285 | A | 8/1996 | Johnson | 2003/0052148 | A1 | 3/2003 | Rajala et al. |
| 5,552,013 | A | 9/1996 | Ehlert et al. | 2003/0066585 | A1 | 4/2003 | McCabe |
| 5,556,504 | A | 9/1996 | Rajala et al. | 2003/0083638 | A1 | 5/2003 | Malee |
| 5,560,793 | A | 10/1996 | Ruscher et al. | 2003/0084984 | A1 | 5/2003 | Glaug et al. |
| 5,602,747 | A | 2/1997 | Rajala | 2003/0089447 | A1 | 5/2003 | Molee et al. |
| 5,624,420 | A | 4/1997 | Bridges et al. | 2003/0135189 | A1 | 7/2003 | Umebayashi |
| 5,628,738 | A | 5/1997 | Suekane | 2004/0016500 | A1 | 1/2004 | Tachibana et al. |
| 5,634,917 | A | 6/1997 | Fujioka et al. | 2005/0000628 | A1 | 1/2005 | Norrley |
| 5,643,165 | A | 7/1997 | Klekamp | 2005/0230056 | A1 | 10/2005 | Meyer et al. |
| 5,643,396 | A | 7/1997 | Rajala et al. | 2005/0230449 | A1 | 10/2005 | Meyer et al. |
| 5,645,543 | A | 7/1997 | Nomura et al. | 2005/0233881 | A1 | 10/2005 | Meyer |
| 5,659,229 | A | 8/1997 | Rajala | 2005/0234412 | A1 | 10/2005 | Andrews et al. |
| 5,660,657 | A | 8/1997 | Rajala et al. | 2005/0257881 | A1 | 11/2005 | Coose et al. |
| 5,683,376 | A | 11/1997 | Kato et al. | 2005/0275148 | A1 | 12/2005 | Beaudoin et al. |
| RE35,687 | E | 12/1997 | Igaue et al. | 2006/0224137 | A1 | 10/2006 | McCabe et al. |
| 5,693,165 | A | 12/1997 | Schmitz | 2006/0265867 | A1 | 11/2006 | Schaap |
| 5,707,470 | A | 1/1998 | Rajala et al. | 2007/0074953 | A1 | 4/2007 | McCabe |
| 5,711,832 | A | 1/1998 | Glaug et al. | | | | |
| 5,745,922 | A | 5/1998 | Rajala et al. | | FOREIGN PATENT DOCUMENTS | | |
| 5,746,869 | A | 5/1998 | Hayden et al. | | | | |
| 5,749,989 | A | 5/1998 | Linman et al. | CA | 1153345 | | 9/1983 |
| 5,788,797 | A | 8/1998 | Herrin et al. | CA | 1190078 | | 7/1985 |
| 5,817,199 | A | 10/1998 | Brennecke et al. | CA | 1210744 | | 9/1986 |
| 5,836,931 | A | 11/1998 | Toyoda et al. | CA | 1212132 | | 9/1986 |
| 5,858,012 | A | 1/1999 | Yamaki et al. | CA | 1236056 | | 5/1988 |
| 5,865,393 | A | 2/1999 | Kreft et al. | CA | 1249102 | | 1/1989 |
| 5,876,027 | A | 3/1999 | Fukui et al. | CA | 1292201 | | 11/1991 |
| 5,879,500 | A | 3/1999 | Herrin et al. | CA | 1307244 | | 9/1992 |
| 5,932,039 | A | 8/1999 | Popp et al. | CA | 1308015 | | 9/1992 |
| 5,964,970 | A | 10/1999 | Woolwine et al. | CA | 1310342 | | 11/1992 |
| 6,000,528 | A * | 12/1999 | van Maanen ............ 198/689.1 | CA | 2023816 | | 3/1994 |
| 6,036,805 | A | 3/2000 | McNichols | CA | 2404154 | | 10/2001 |
| 6,050,517 | A | 4/2000 | Dobrescu et al. | CA | 2541194 | | 1/2006 |
| 6,074,110 | A | 6/2000 | Verlinden et al. | CA | 2559517 | | 5/2007 |
| 6,098,249 | A | 8/2000 | Toney et al. | DE | 102006047280 | | 4/2007 |
| 6,123,792 | A | 9/2000 | Samida et al. | EP | 0048011 | | 3/1982 |
| 6,170,636 | B1 * | 1/2001 | Een et al. ................ 198/471.1 | EP | 0089106 | | 9/1983 |
| 6,183,576 | B1 | 2/2001 | Couillard et al. | EP | 0304140 | | 8/1987 |
| 6,210,386 | B1 | 4/2001 | Inoue | EP | 0439897 | | 2/1990 |
| 6,306,122 | B1 | 10/2001 | Narawa et al. | EP | 0455231 | | 11/1991 |
| 6,309,336 | B1 | 10/2001 | Muessig et al. | EP | 510251 | | 10/1992 |
| 6,312,420 | B1 | 11/2001 | Sasaki et al. | EP | 0652175 | | 5/1995 |
| 6,314,333 | B1 | 11/2001 | Rajala et al. | EP | 0901780 | | 3/1999 |
| 6,315,022 | B1 | 11/2001 | Herrin et al. | EP | 1132325 | | 9/2001 |
| 6,336,921 | B1 | 1/2002 | Kato et al. | EP | 1272347 | | 1/2003 |
| 6,358,350 | B1 | 3/2002 | Glaug et al. | EP | 1707168 | | 4/2006 |
| 6,369,291 | B1 | 4/2002 | Uchimoto et al. | ES | 509706 | | 11/1982 |
| 6,375,769 | B1 | 4/2002 | Quereshi et al. | ES | 520559 | | 12/1983 |
| 6,391,013 | B1 | 5/2002 | Suzuki et al. | ES | 296211 | | 12/1987 |
| 6,416,697 | B1 | 7/2002 | Venturino et al. | FR | 2891811 | | 4/2007 |
| 6,473,669 | B2 | 10/2002 | Rajala et al. | GB | 191101501 | | 1/1912 |
| 6,475,325 | B1 | 11/2002 | Parrish et al. | GB | 439897 | | 12/1935 |
| 6,478,786 | B1 | 11/2002 | Gloug et al. | JP | 428364 | | 5/1990 |
| 6,482,278 | B1 | 11/2002 | McCabe et al. | JP | 6197925 | | 1/1991 |
| 6,494,244 | B2 | 12/2002 | Parrish et al. | JP | 542180 | | 5/1991 |
| 6,521,320 | B2 | 2/2003 | McCabe et al. | JP | 626161 | | 5/1991 |
| 6,551,228 | B1 | 4/2003 | Richards | JP | 576566 | | 9/1991 |
| 6,551,430 | B1 | 4/2003 | Glaug et al. | JP | 626160 | | 7/1992 |
| 6,554,815 | B1 | 4/2003 | Umebayashi | JP | 10-277091 | | 4/1997 |
| 6,596,108 | B2 | 7/2003 | McCabe | SE | 0602047 | | 6/2007 |
| 6,605,172 | B1 | 8/2003 | Anderson et al. | WO | WO9907319 | | 2/1999 |

| | | | | | | |
|---|---|---|---|---|---|---|
| WO | WO9913813 | 3/1999 | | WO | WO0172237 | 10/2001 |
| WO | WO9965437 | 12/1999 | | WO | WO05075163 | 1/2005 |
| WO | WO0143682 | 6/2001 | | | | |

* cited by examiner

ARTICLE TRANSFER AND PLACEMENT APPARATUS

BACKGROUND OF THE INVENTION

This invention related to an apparatus for transferring articles such as absorbent pads in the manufacture of disposable absorbent articles such as diapers, incontinence control garments or female sanitary pads as they advance along a production line.

In the production and manufacture of disposable products such as sanitary napkins or pants-type diapers, it frequently becomes necessary to manufacture a component of the product in one orientation, and then to rotate that component part 90° so that it is suitably oriented for use in another step in the production process. Various devices have been developed for this purpose and are known to those experienced in the industry. Examples of such apparatus are those described in U.S. Pat. Nos. 4,726,876, 4,880,102, and 5,025,910.

As discussed above, a typical article to be reoriented by the apparatus of this invention is an absorbent pad. Because absorbent pads are typically comprised of several webs, an absorbent core and several elastic members, there is a tendency of these assemblies to contract and become distorted during transfer operations.

An example of a device developed for this purpose is described in U.S. Pat. No. 6,648,122. In this patent, an apparatus is described which receives inserts at an infeed point, stretched them in the cross-direction to what is a more normal length, and then places them onto a receiving web. However this apparatus has the limitation of receiving and placing the inserts at similar product pitches, or web velocities. Additionally, as stated above, this apparatus is only able to stretch the inserts in a cross-direction.

It is desirable to have an apparatus which is capable of receiving items at one pitch, while placing them onto a receiving conveyor at a second pitch in order to provide more flexibility in the range of product configurations. It is also desirable to have an apparatus which is capable of stretching an item in both the cross direction and the machine direction.

SUMMARY OF THE INVENTION

The apparatus of the presenting invention is provided with the capability of receiving inserts at one pitch, while placing them onto a receiving conveyor at a second pitch. This allows for the placement of very short inserts onto relatively wide products, or long inserts onto relatively narrow products. This flexibility provides the user with the option of designing a wide range of product configurations in response to market demands.

The apparatus uses servo-motor electronic cam profiling to match web velocities at the pick-up and lay-down points. An additional benefit of this new design lies in the fact that you can manipulate the exact motion profiles to optimize transfers. This is a particularly useful tool in that inserts can be manipulates to stretch them nominally in both the cross and machine directions, thereby reducing the amount of wrinkling which might occur as the stretched elastic members are handed off from one device to the next.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
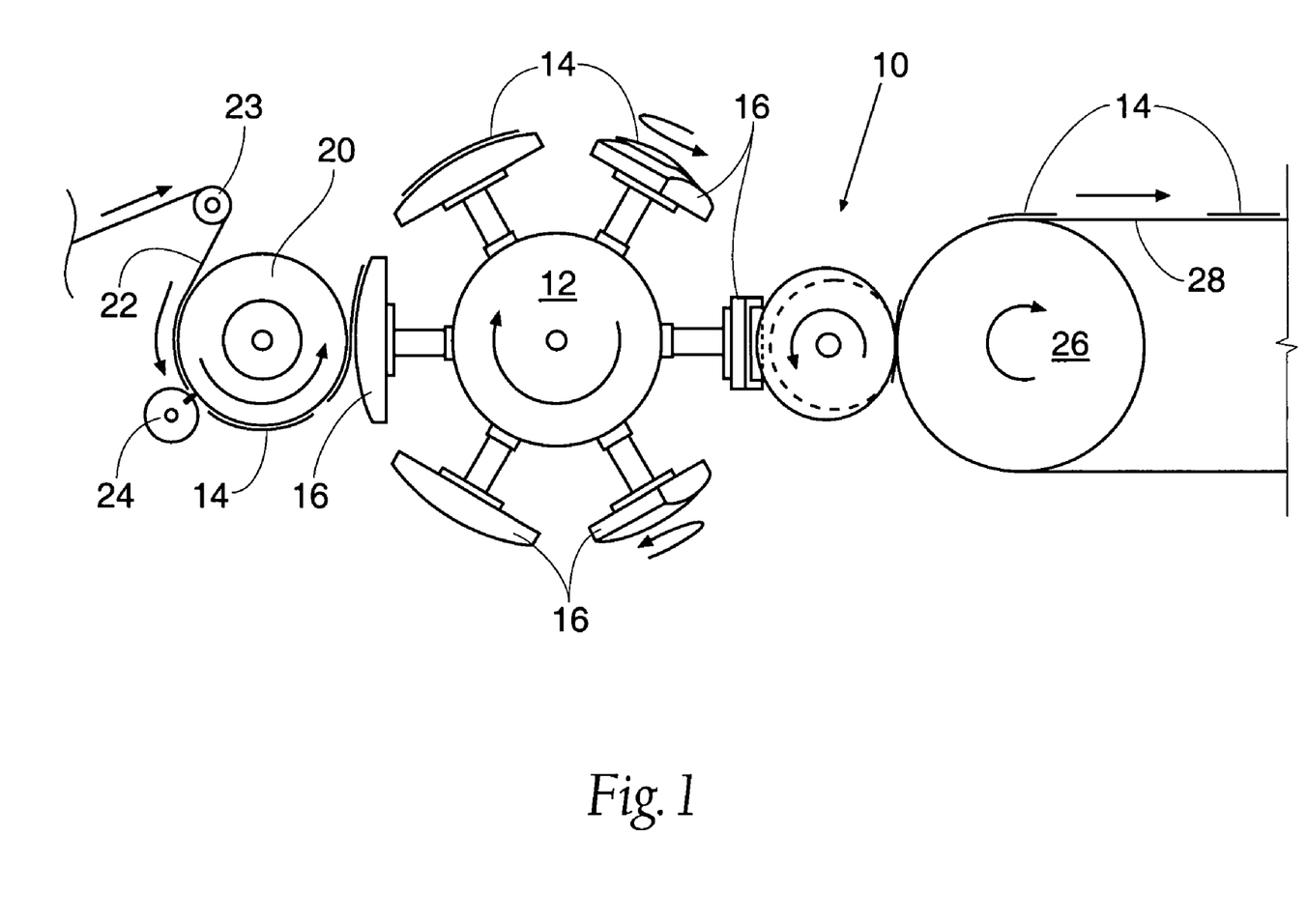
FIG. 1 is a fragmentary side elevation view, shown in somewhat diagrammatic form, of a pad transferring assembly of this invention.

Referring more particularly to the drawings, there is seen in FIG. 1 a transfer device 10 of the present invention. The transfer device 10 is adapted to receive a series of articles from a pad turning device 12 which includes a plurality of radially extending transfer heads 16. The pad turning device 12 may be, for example, a rotary pad turner of the type more fully described in U.S. Pat. No. 5,025,910. The articles 14, such as absorbent pads, may be any elongated articles which need to be rotated 90° during the course of a manufacturing operation. Such pad turning devices 12 are especially needed and are suited for use in connection with the manufacture and packaging of sanitary napkins as well as absorbent pads which are used in the assembly of disposable garments such as adult incontinence garments or children's training pants.

Also seen in FIG. 1, articles 14 are successively and individually picked-up by the transfer heads 16 of the pad transfer device 12. In the illustrated embodiment, the pads 14 are picked up from a vacuum drum 20 which is provided for use, in the nature of an anvil, for cutting a web 22 of absorbent material into individual pads 14 utilizing a rotary cutting device 24 of a type well known in the art. Various conventional conveying and direction changing devices such as rollers may be employed in the feeding of the web and do not form a part of this invention.

After the articles 14 have been rotated 90 degrees, they are picked-up by the transfer device 10 of this invention. In this sense, a canted pitch changer 43 is provided which stretches the articles 14, as will be described below, and deposits them in that condition onto another conveyor 28 as it travels around the outer surface of a drum 26. A conveyor 28 transports the articles 14 for further processing or to a packaging device, as required by a particular application.

Figure 2:
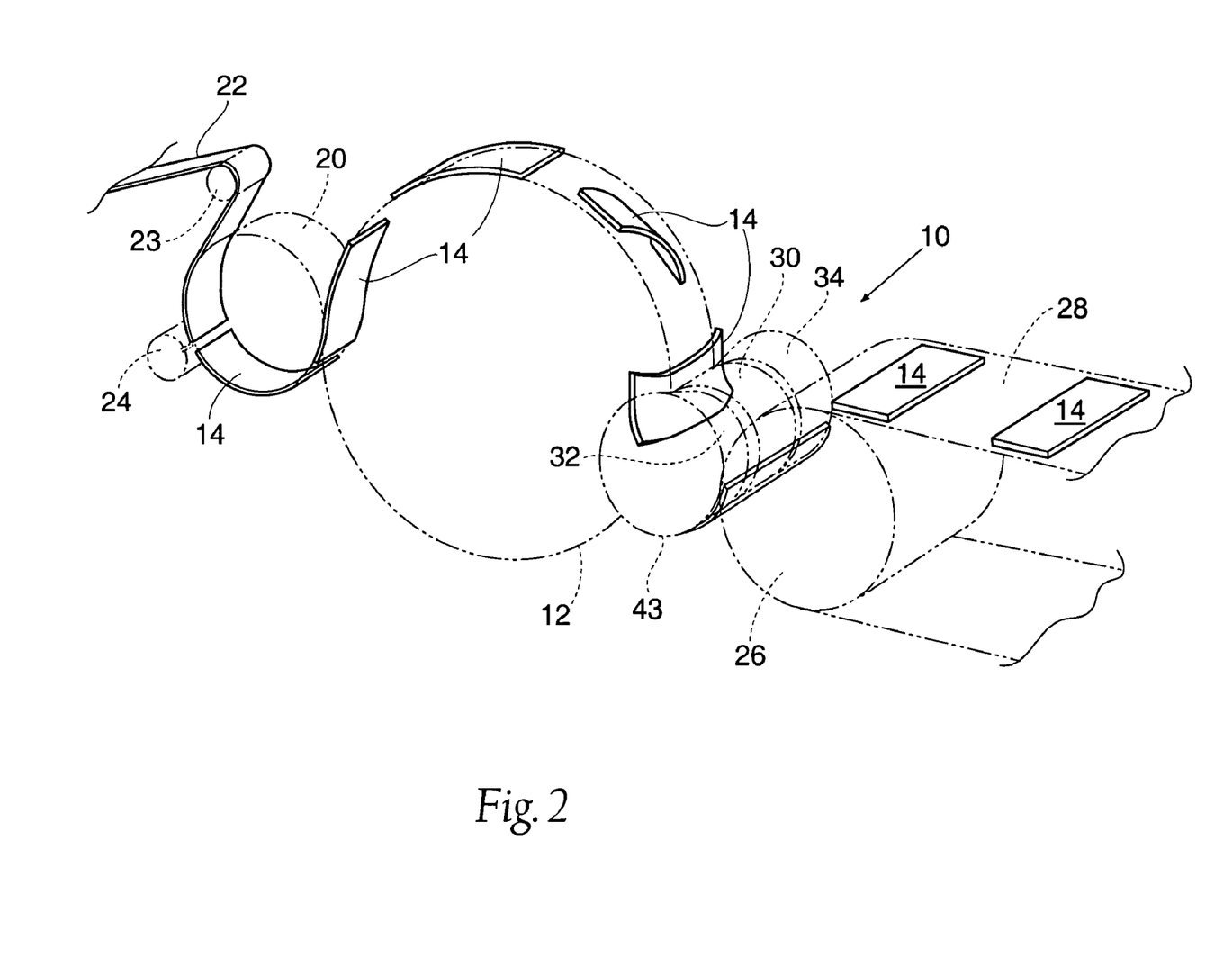
FIG. 2 is a perspective fragmentary, diagrammatic view, showing the related apparatus by means of phantom lines and illustrating the path of movement of pads moving in accordance with the invention.

Referring to FIG. 2, there is seen a diagrammatic depiction of the travel path of the web 22 and the resultant pads 14 which are formed therefrom. In this depiction the various apparatus have been eliminated but are partially illustrated by means of phantom lines.

Figure 3:
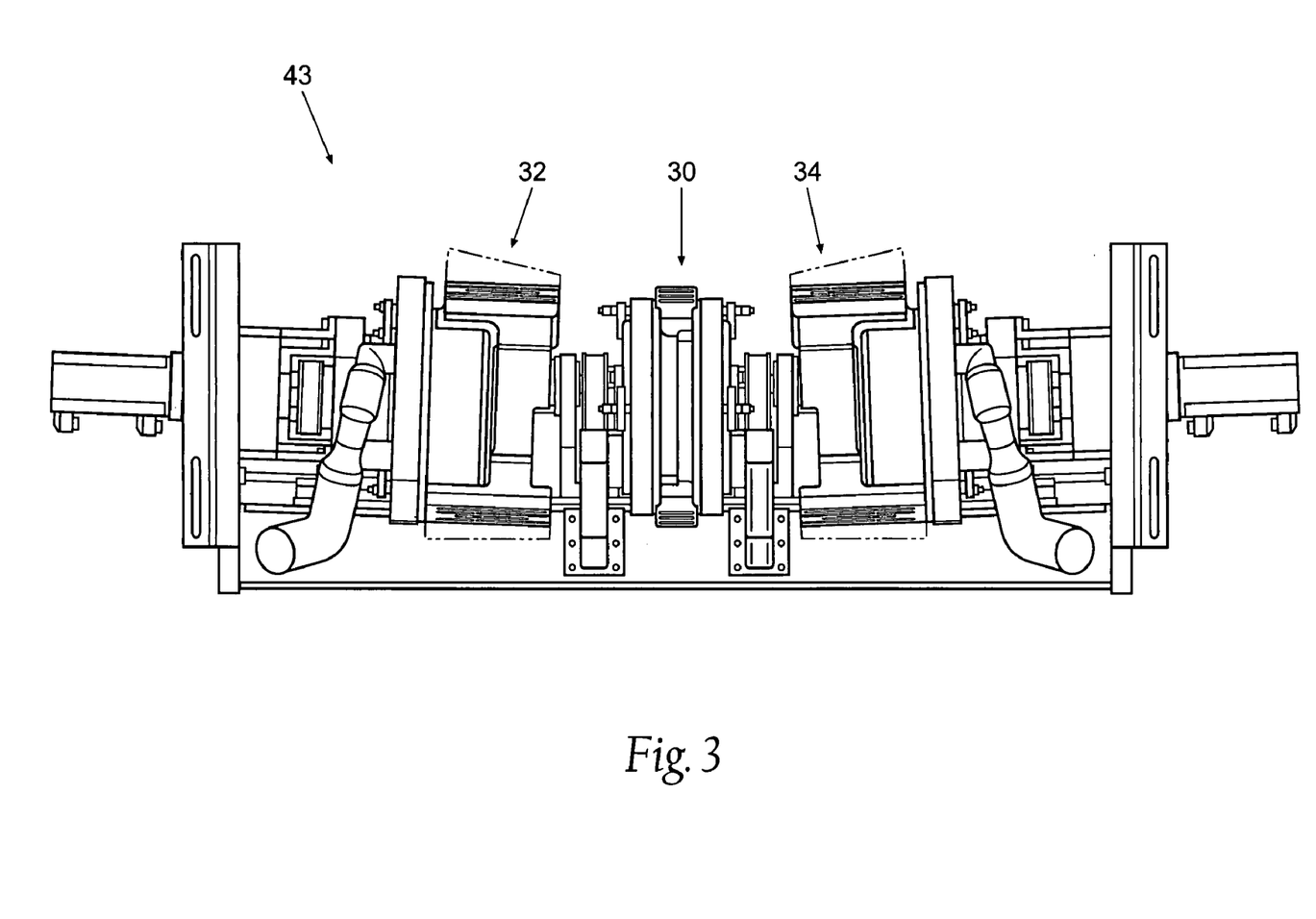
FIG. 3 is a bottom view of the apparatus of the invention.
Figure 4:
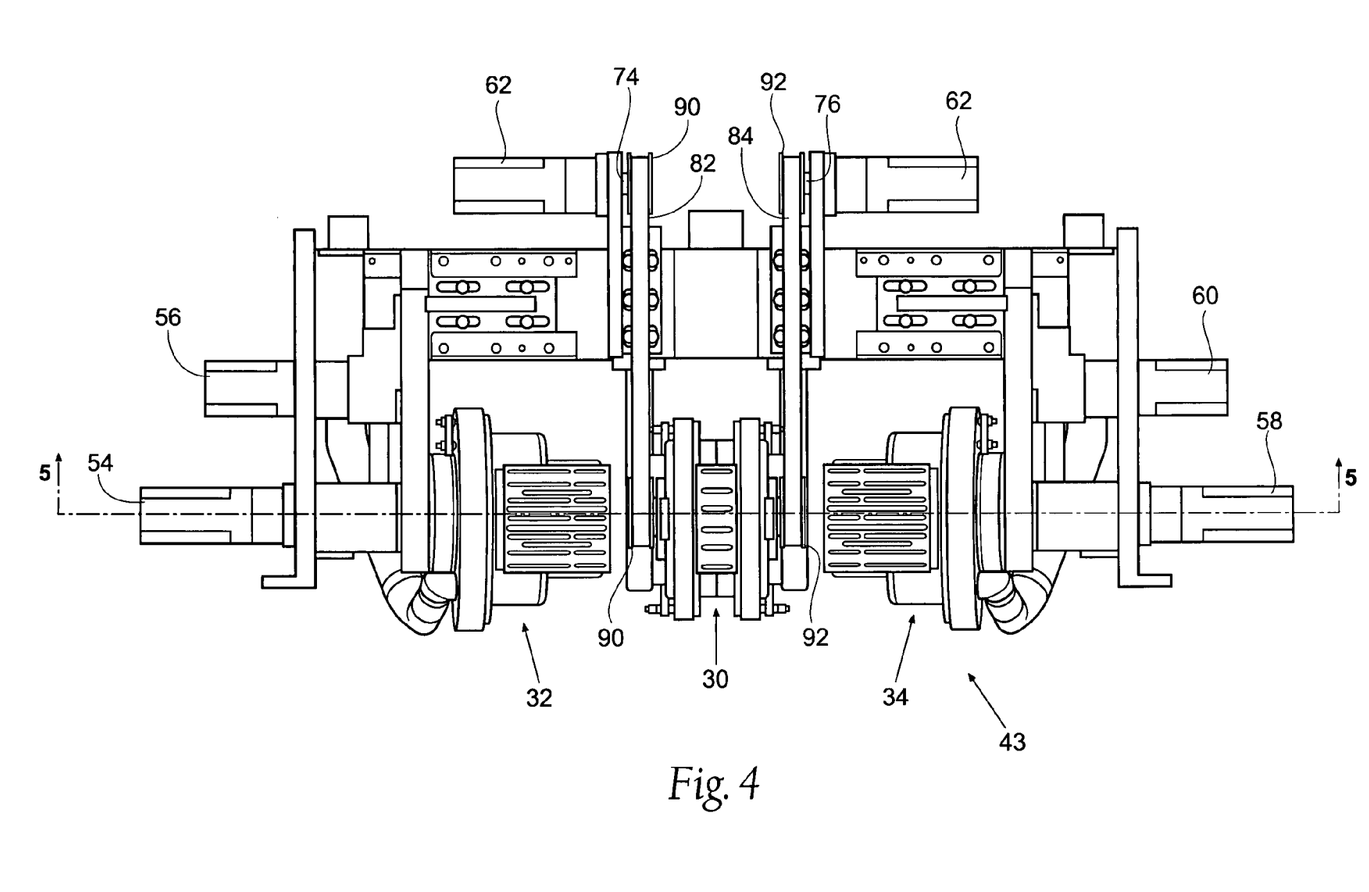
FIG. 4 is a side elevation view of the apparatus of the invention.

The article transfer device 10, and particularly the canted pitch changer 43 of this invention is more fully shown in FIGS. 3-4.

As shown in FIG. 3, the transfer device 10, and canted pitch changer 43 includes a central cylindrical section 30 and a pair of canted outboard sections 32, 34. The center cylindrical section 30 is adapted to hold and transfer the center of the article 14. The canted outboard sections 32, 34 are in the form of truncated cones which have their central rotational axis at an oblique angle relative to the central cylindrical section 30.

Due to this oblique angle the surfaces of the outboard sections 32, 34 slope toward the center cylindrical section 30 at the pad acquisition point. However, the surfaces of the outboard sections 32, 34 and the central section 30 come into approximate alignment with each other at the opposite side of the device, i.e. the pad drop off point. This configuration causes the pads 14 to be stretched in a lengthwise direction as the pad 14 is rotated from the pad acquisition point to the pad drop off point.

Figure 5:
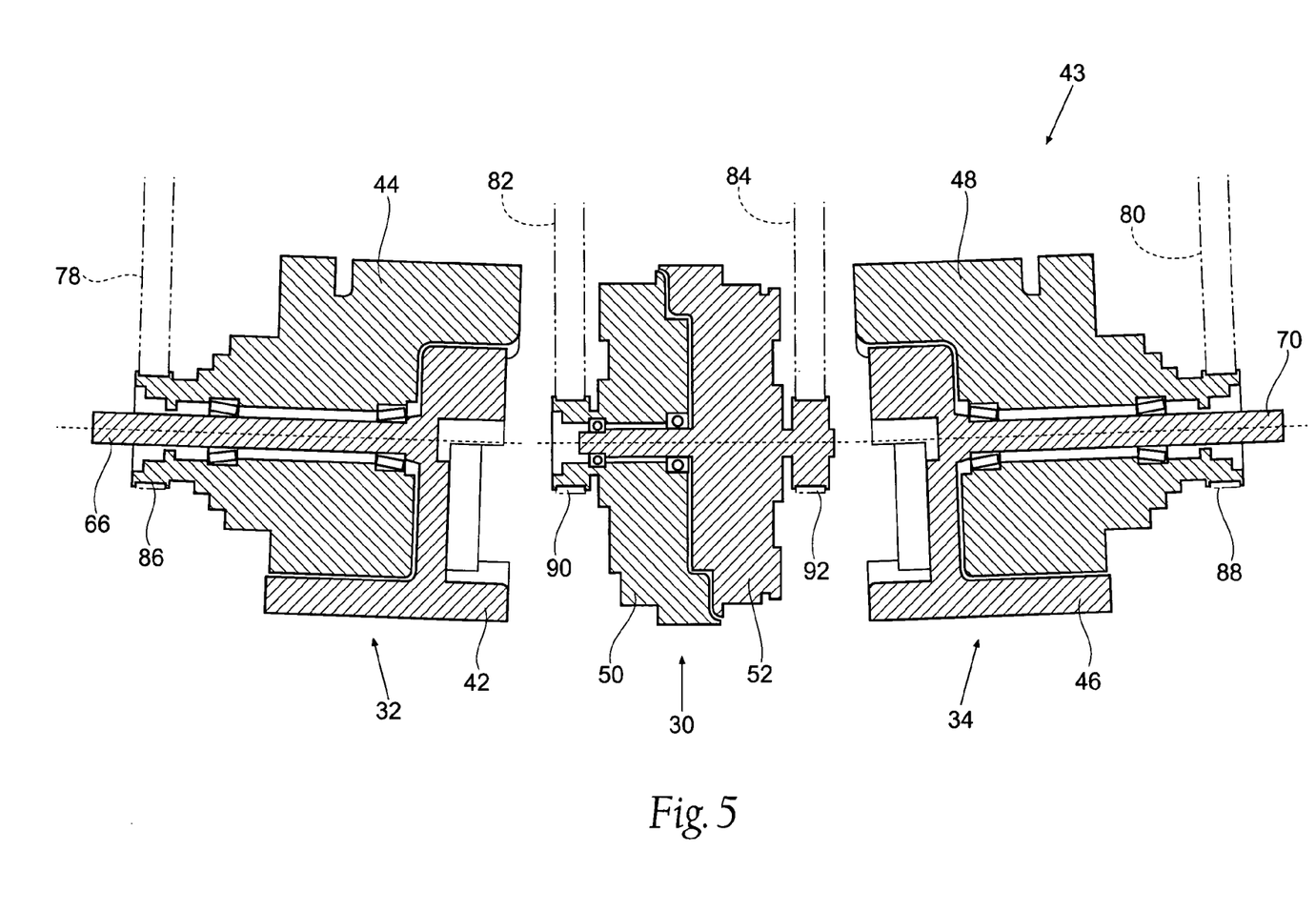
FIG. 5 is a simplified cross sectional view of the apparatus of the invention.

Further, as is best shown in FIG. 5, each of the center section 30 and the outboard sections 32, 34 is comprised of two separately driven segments. The separately driven segments have two advantages. First, a velocity differential between the center section 30 and outboard sections 32, 34 can be utilized to stretch the pads 14 in the cross-machine direction. Second, each segment of each section can be driven at a different velocity, such that the transfer device can be placing a first pad 14 at a first velocity at the same time a second pad 14 is being acquired at a second velocity.

In use, the transfer apparatus 10 rotates from the position adjacent the transfer heads 16 wherein the surfaces of the outboard sections 32, 34 and the center section 30 are in their most concave position, to their linear orientation at the drop-off point, the pads 14 which are being transported are each successively stretched and pulled to their maximum length. If the outboard sections 32, 34 are driven at a different velocity than the center section 30, the pads 14 will also be stretched in the cross-machine direction.

As is well known in the art, each of the segments is connected internally to a source of vacuum. A pattern of holes is provided on the surface of each segment through which the internal vacuum acts to draw the pads 14 towards the surface. The center section 30 may be provided with a surface having a greater coefficient of friction than the surfaces of the outboard sections 32, 34. Therefore, the ends of the articles 14 are able to slip across the faces of the outboard sections 32, 34 when the pad-extending tensile forces exceed the force required to overcome the effects of friction. The higher coefficient of friction of the center section 30 prevents the transferred article 14 from being pulled off the centerline of the device 10. For example, the surface of the center section 30 may be formed of a low durometer silicone rubber while the surface of the outboard sections 32, 34 may be formed of stainless steel.

Referring again to FIG. 5, the left outboard 32 section is comprised of an inner segment 42 and an outer segment 44. The right outboard section 34 is also comprised of an inner segment 46 and an outer segment 48. Each segment is separately movable and driven by a servo motor. Referring first to the left outboard section 32, the outer segment 44 is driven by a first servo motor 54 which is connected directly to the outer segment 44 by a first drive shaft 66. The inner segment 42 is connected to a second servo motor 56 by a first set of sprockets 86 and a first belt 78. Likewise, referring to the right outboard section 34, the outer segment 48 is driven by a third servo motor 58 which is directly connected to the outer segment 48 by a third drive shaft 70, while the inner segment 46 is connected to its fourth servo motor 60 by a second set of sprockets 88 and a second belt 80.

The center section 30 is comprised of a first center segment 50 and a second center segment 52. Each segment 50, 52 is separately movable and driven by a servo motor 62, 64 which is connected to the segment 50, 52 by a belt and a set of sprockets 90, 92. The first center segment 50 is driven by a fifth servo motor 62 via a third set of sprockets 88 and a third belt 82. The second center segment 52 is driven by a sixth servo motor 64 via a fourth set of sprockets 92 and a fourth belt 84.

The two segments which makes up each section could be driven by a single servo motor, but preferably, each of the segments is be separately driven so that one can be picking up articles at one velocity, while the other is depositing the articles at a different velocity. Having each outboard section 32, 34 and the center section 30 being separately driven allows the outboard sections 32, 34 and the center section 30 to be driven at different velocities. This velocity differential will allow for stretching the article 14 in the cross-machine direction. This is significant in that stretching the product reduces the amount of wrinkling which may occur as the stretched member are handed off from one device to the next.

Likewise, each segment could be driven by a mechanical drive means capable of producing the velocity changes. Eccentric or other non-circular gears could produce such a velocity changing source of power. However, servo motors are the preferred means, as they provide programmability, flexibility, and isolation of torque disturbances. A preferred embodiment of this invention uses separate drives for each of the six segments. Additional embodiments might use more than three sections, or any reasonable number of segments.

It is clear that this technology can be applied to the transfer and placement of many different types of articles in the disposable goods industry and other industries as well.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. Apparatus for transferring articles from a first moving conveying device and depositing said articles onto a second moving conveyor, comprising:

a central vacuum drum having a longitudinal central axis and being disposed to acquire and transport a central portion of an article to be transferred;

a pair of canted outboard vacuum drums, each comprising a truncated cone having a central rotational axis disposed at an oblique angle relative to that of said central vacuum drum and adapted to acquire and transport the ends of said article, wherein, due to said oblique angle faces of the outboard drums are sloped toward the center of the article, wherein, due to said oblique angle faces of the outboard drums are sloped toward the center of the article at its acquisition point and are parallel to and generally in a plane with the face of the central drum at the deposition point;

said central drum and each of said outboard drums being independently rotatable and independently controlled.

2. Apparatus according to claim 1 wherein each of said drums comprises two separate segments.

3. Apparatus according to claim 2 wherein each drum segment is independently rotatable and independently controlled.

4. Apparatus for picking up an article from the periphery of a generally toroidal surface, stretching said article to a fully extended condition, rotating said article 180° and placing it on a flat moving conveyor surface comprising:

a central vacuum drum disposed to acquire and transport a central portion of an article to be transferred;

a pair of canted outboard vacuum drums, each comprising a truncated cone with an inboard diameter smaller than its outside diameter and having a central rotational axis disposed at an oblique angle relative to that of said central vacuum drum and being adapted to acquire and transport the ends of said article, wherein said oblique angle is such that the faces of the outboard drums are sloped toward the center of the article at its acquisition point and are approximately parallel to and generally in plane with the face of the central drum at the deposition point;

said central drum and each of said outboard drums being independently rotatable and independently controlled.

5. Apparatus for successively rotating and transferring articles traveling in an array of discrete articles comprising:
   a rotatable drive means including a rotatable hub having a plurality of transfer head assemblies mounted thereon for rotation of the transfer heads around a closed path passing through an acquisition zone where articles are picked up and a discharge zone;
   a plurality of radially extending supports disposed around the rotatable hub, each supporting a convexly shaped first transfer device mounted transversely to its respective one of said supports and a rotatable axis of said support;
   a second transfer device located at said discharge zone and being adapted to successively receive articles of said array of discrete articles from said first transfer devices; said second transfer device located at said discharge zone and being adapted to successively receive article of said array of discrete articles from said first transfer devices;
   said second transfer device comprising a central vacuum drum disposed to acquire and transport a central portion of an article to be transferred and a pair of canted outboard vacuum drums, each being in the shape of a truncated cone having a central rotational axis disposed at an oblique angle relative to that of said central vacuum drum and adapted to acquire and transport the ends of said article, wherein said oblique angle is such that the faces of the outboard drums are sloped toward the center of the article at its acquisition point and are approximately parallel to and generally in a plane with the face of the central drum a the deposition point;
   said central drum and each of said outboard drums being independently rotatable and independently controlled.

6. Apparatus according to claim 5 wherein each of said drums comprises two separate segments.

7. Apparatus according to claim 6 wherein each drum segment is independently rotatable and independently controlled.

8. Apparatus for acquiring a succession of transversely oriented articles from a rotary device, rotating, extending the length of said articles and transferring said articles to a flat conveyor, comprising:
   a center vacuum drum section, disposed to acquire and carry the center of each successive article to be transferred;
   a pair of outboard canted vacuum drums, each drum comprising a truncated cone section and disposed so as to acquire and carry an end of each successive product, wherein the angle of cant is such that at the point of most acute angle, the faces of the vacuum drum are approximately parallel to the ends of a presented article at its acquisition point and are parallel to and generally in plane with the face of the center vacuum drum section at the deposition point;
   said central vacuum drum and each of said outboard drums being independently rotatable and independently controlled.

9. Apparatus according to claim 8 wherein each of said drums comprises two separate segments.

10. Apparatus according to claim 9 wherein each drum segment is independently rotatable and independently controlled.

* * * * *